United States Patent [19]

Marshall et al.

[11] 4,209,611
[45] Jun. 24, 1980

[54] DIHYDROSTEFFIMYCIN COMPOUNDS

[75] Inventors: Vincent P. Marshall; David W. Elrod; Paul F. Wiley, all of Portage, Mich.

[73] Assignee: The Upjohn Company, Kalamazoo, Mich.

[21] Appl. No.: 27,878

[22] Filed: Apr. 6, 1979

[51] Int. Cl.$^2$ .............................................. C07H 15/24
[52] U.S. Cl. .................................. 536/17 A; 424/180; 424/181; 435/78
[58] Field of Search .............................. 536/17 A, 17

[56] References Cited

U.S. PATENT DOCUMENTS

| | | | |
|---|---|---|---|
| 3,309,273 | 3/1967 | Bergy et al. | 536/17 A |
| 3,794,721 | 2/1974 | Brodasky et al. | 424/120 |
| 3,976,667 | 8/1976 | Kelly | 536/17 A |

*Primary Examiner*—Johnnie R. Brown
*Attorney, Agent, or Firm*—Roman Saliwanchik

[57] ABSTRACT

Antibiotics 10-dihydrosteffimycin (U-58,875), and 10-dihydrosteffimycin B (U-58,874) are produced by carbon 10 ketonic carbonyl reduction in fermentation processes using the known antibiotics steffimycin and steffimycin B, respectively, as starting materials. These novel antibiotics are active against various microorganisms, for example, *Bacillus subtilis, Bacillus cereus, Sarcina lutea, Streptococcus pyogenes,* and *Mycobacterium avium.* Thus, these antibiotics can be used to inhibit the growth of the above microorganisms in various environments.

8 Claims, No Drawings

DIHYDROSTEFFIMYCIN COMPOUNDS

The invention described herein was made in the course of, or under Contract NO1-CM-77100 with the Division of Cancer Treatment, National Institutes of Health, Department of Health, Education and Welfare, Bethesda, Maryland 20014.

BACKGROUND OF THE INVENTION

The process for preparing the antibiotic steffimycin, and the description of its various biological properties, are disclosed in U.S. Pat. No. 3,309,273. The antibiotic at that time was known as steffisburgensimycin.

The process for preparing steffimycin B and its characterization are disclosed in U.S. Pat. No. 3,794,721.

The structures of steffimycin and steffimycin B can be shown as follows:

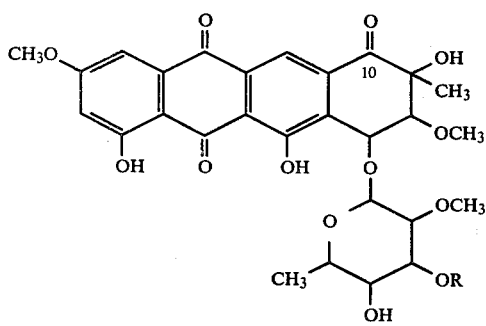

R = H (Steffimycin)
R = CH₃ (Steffimycin B)

BRIEF SUMMARY OF THE INVENTION

Antibiotic 10-dihydrosteffimycin can be prepared in a fermentation process using the known microorganism *Actinoplanes utahensis*, NRRL 5614. This microorganism is described in U.S. Pat. No. 3,824,305. The description of the microbe in said patent is incorporated herein by reference to said patent. 10-Dihydrosteffimycin is prepared in the fermentation by the addition of steffimycin to the fermentation.

The antibiotic 10-dihydrosteffimycin B also can be prepared in a fermentation using *Actinoplanes utahensis*, NRRL 5614, or the novel microbe Chaetomium sp. (BB 427) NRRL 11442. This antibiotic is produced in said fermentations by the addition of steffimycin B to the fermentation.

The novel antibiotics of this invention are recovered from the fermentation beers using a series of filtration, extraction, and thin layer chromatography (tlc) procedures.

DETAILED DESCRIPTION OF THE INVENTION

The Novel Antibiotics

10-Dihydrosteffimycin and 10-dihydrosteffimycin B have the following structures:

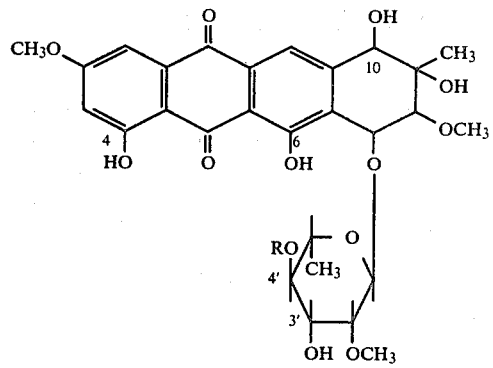

R = H (10-Dihydrosteffimycin)
R = CH₃ (10-Dihydrosteffimycin B)

The Microorganisms

*Actinoplanes utahensis*, NRRL 5614, is a known microorganism deposited at the Northern Regional Research Laboratory, U.S. Department of Agriculture, Peoria, Illinois, U.S.A. A subculture of this microorganism can be obtained from this repository upon request. This microorganism is characterized in U.S. Pat. No. 3,824,305.

Chaetomium sp. (BB 427) is a biologically pure culture of a novel microorganism. A subculture has been deposited in the permanent collection at the Northern Regional Research Laboratory, U.S. Department of Agriculture, Peoria, Illinois, U.S.A. Its accession number in this repository is NRRL 11442. A subculture of this microorganism can be obtained from the repository upon request. It should be understood that the availability of the culture does not constitute a license to practice the subject invention in derogation of patent rights granted with the subject instrument by governmental action. The taxonomic description of Chaetomium sp. (BB 427), NRRL 11442, as determined by Alma Dietz and Grace Li of the Upjohn Research Laboratories, follows.

Chaetomium sp. (BB 427) NRRL 11442 is both culturally and morphologically within the limits outlined for the Chaetomiaceae by Ames [Ames, L. M. 1963. A monograph of the Chaetomiaceae. U.S. Army Res. Dev. Ser. 2: i-ix, 1-125.].

Color: Aerial growth lavender-gray to olive-gray. Reverse growth cream to gray-brown. See Table 1. Reference colors are given in Table 2.

Micromorphology: Perithecia spherical, yellowish-brown. Terminal hairs long, straight to flexuous, becoming open-spiraled. Surface of terminal hairs rough by light microscopy (LM) and open-pustuled by scanning electron microscopy (SEM). Asci irregularly club-shaped. Ascospores appear to contain a large refractive globule when observed by LM. They appear hat-shaped when observed in side view by SEM (like the half of a fruit on one side—which may give the refractive globule appearance by LM—and inflated on the other side). The surface is smooth. Chlamydospores are numerous. Lateral and terminal hairs become septate.

Chaetomium spp. have received much attention because of their ability to decompose cellulose. In attempting to characterize the strain cited, we have compared our data with observations recorded by Ames (supra), Hawksworth and Wells [Hawksworth, D. L., and H. Wells. 1973. Ornamentation on the terminal hairs in Chaetomium Kunze ex Fr. and some allied genera. Mycol. Pap. 134: 1-24. Kew: Commonwealth Mycological Institute.], Millner [Millner, P. D. 1977. Radial growth responses to temperature by 58 Chaetomium species, and some taxonomic relationships. Mycologia. LXIX: 492-502.], Millner et al. [Millner, P. D., J. J. Motta, and P. L. Lentz. 1977. Ascospores, germ pores, ultrastructure, and thermophilism of Chaetomium. Mycologia. LXIX: 720-733.], and Udagawa and Cain [Udagawa, S., and R. F. Cain. Some new or noteworthy species of the genus Chaetomium. 1969. Can. J. Bot. 47: 1939-1951.]. Excellent descriptions and illustrations are given in the references cited. Our culture does not match any of them.

Hawksworth and Wells (supra) have attempted a modern system for classifying Chaetomium and related genera based on perithecia type, ascus type, ascospore type, and terminal hair ornamentation type. Using this system we described our species as follows:

Perithecia—Type 1: Globose, subglobose or ovate.
Ascus shape—Type 1: Clavate or pyriform (ascospores irregularly arranged).
Ascospore type—Type III: Uniapiculate; ovate or globose with a distinctly pointed end ('almond-shaped').
Terminal hair ornamentation—Type II—Cupulate. Type III—Annulate. Type V—Lacerate.

Millner (supra) has grouped Chaetomium species based on growth in different temperature ranges. Cultures growing at 15°-37° C. are transitional mesophiles; those growing at 15°-40° C. are microthermophiles. Our culture was grown at 18°, 24°, 28°, 32°, 37°, 45°, and 55° C. It did not grow at 45° or 55° C. Therefore, it may be considered a transitional mesophile and possibly a microthermophile. Growth was excellent at 37° C. It is quite likely that growth would occur at 40° C.

We conclude that Chaetomium sp. NRRL 11442 is a new species. It does not resemble any of the species in the references cited.

Table 1

Appearance of Chaetomium sp. NRRL 11442 on Six Agar Slant Media*

| Agar Medium | Determination | NRRL 11442 |
|---|---|---|
| Neopeptone-dextrose agar** | S | Pale gray white with black overgrowth |
| | R | Cream to light gray brown |
| Czapek's sucrose agar (Difco dehydrated agar) | S | Pale gray white with brown overgrowth |
| | R | Cream-brown |
| Leonian's agar** | S | Pale olive-gray |
| | R | Cream-gray brown |
| Water agar** | S | Very poor olive-gray |
| | R | Gray under growth |
| Potato dextrose agar (Difco dehydrated agar) | S | Olive-cream-white |
| | R | Cream with slight brown color at bottom of tube |
| Gray's agar** | S | Lavender-gray with slight brown over growth |
| | R | Cream brown |

S = Surface
R = Reverse
*Pyke, T.R., and A. Dietz. U-21,963, a new antibiotic. I. Discovery and biological activity. Appl. Microbiol. 14: 506-510.
**Cooke, W.B. 1963. A laboratory guide to fungi in polluted waters, sewage, and sewage treatment systems, their identification and culture. U.S. Public Health Serv. Publ. 999-WP-1.
***g/liter distilled water: glucose, 30.0; yeast extract, 7.0; KH$_2$PO$_4$, 5.0, agar, 15.0.

Table 2

Reference Color Characteristics of Chaetomium sp. NRRL 11442*

| Agar Medium | Determination | NBS Chip No. | NBS Color |
|---|---|---|---|
| Czapek's sucrose | S with trace | 96. d.Ol Br. 263. White | Dark olive-brown with trace white |
| | R | 96. d.Ol Br.-center | Dark olive-brown |
| | | 91. d.gy.Y-edge | Dark grayish yellow |
| | P | 90. gy.Y | Grayish yellow |
| Water agar | S | 113. Ol Gy | Olive-gray |
| | R | 113. Ol Gy | Olive-gray |
| | P | — | — |
| Potato dextrose agar | S | 109. l.gy.Ol | Light grayish olive |
| | R | 110. gy. Ol | Grayish olive |
| | P | 105. gy.g Y | Grayish greenish yellow |
| Gray's agar | S with trace | 111. d.gy.Ol 263. White | Dark grayish olive with trace white |
| | R with trace | 110. gy. Ol 87. m. Y | Grayish olive with trace moderate yellow |
| | P | 87. m. Y | Moderate yellow |

S = Surface
R = Reverse
P = Pigment
*SRM 2107. Color Kit. Consists of: SRM 2106, ISCC-NBS Centroid Color Charts, and SP 440, Color: Universal Language and Dictionary of Names. Office of Std. Ref. Material, Room B311, Chem. Bldg., Nat. Bur. of Stds., Wash., D.C. 20234.

The bioconversions of the subject invention are carried out by growing the disclosed microorganisms is an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distiller's solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation medium since tap water and unpurified ingredients are used as components of the medium prior to sterilization of the medium.

The bioconversion processes can be effected at any temperature conducive to satisfactory growth of the particular microorganism, for example, between about 18° and 40° C., and preferably between about 20° and 28° C. The medium normally remains neutral during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the bioconversion process and the attendant inefficient utilization of the equipment. Accordingly, it is desirable to produce a vegetative inoculum in a nutrient broth culture by inoculating this broth culture with an aliquot from a soil stock, an agar plug stored above liquid N$_2$, or a slant culture.

When a young, active vegetative inoculum has thus been secured, it is transferred aseptically to large vessels or tanks. The medium in which the vegetative inoculum is produced can be the same as, or different from, that utilized for the bioconversion process, so long as good growth of the microorganism is obtained.

Steffimycin and steffimycin b can be added to their respective fermentations, advantageously, as dimethylformamide solutions (25 mg/l), or as a milled aqueous suspension, to a final medium concentration of about 1 to 100 mg/l, advantageously, to about 25 mg/l. The addition of these compounds to the fermentations can be done at any time after suitable growth of the microbe is evidenced and, advantageously, between about 36 and about 48 hours of fermentation time.

A variety of procedures can be employed in the isolation and purification of the compounds produced by the subject invention, for example, solvent extraction, partition chromatography, silica gel chromatography, liquid-liquid distribution in a Craig apparatus, adsorption on resins, and crystallization from solvents.

In a preferred recovery process the compounds are recovered from the culture medium by separation of the mycelia and undissolved solids by conventional means, such as by filtration or centrifugation. The antibiotic is recovered from the filtered or centrifuged broth by extraction with a suitable solvent for the antibiotic. The solvent extract containing the desired antibiotic is concentrated and then subjected to purification procedures as disclosed infra.

After recovery of the antibiotic from the bioconversion fermentation beer, the recovery preparation is then subjected to purification procedures which will ultimately yield a purified crystalline preparation of the antibiotic.

The crude preparation of the antibiotic can be subjected to chromatographic procedures on silica gel. The chromatographic column can be eluted with a suitable solvent system, for example, $CHCl_3$—MeOH (97:3).

Active fractions from the above chromatographic procedure can be subjected to another similar chromatographic procedure to obtain the antibiotic in its essentially pure form.

The following examples are illustrative of the processes of the subject invention but are not to be construed as limiting. All percentages are by weight and all solvent mixture proportions are by volume unless otherwise noted.

EXAMPLE 1—Bioconversion Of Steffimycin To 10-Dihydrosteffimycin

Part A. Fermentation

The microorganism Actinoplanes utahensis, NRRL 5614 is maintained in a sterile soil. This biologically pure culture is used to inoculate a series of 500-ml Erlenmeyer flasks, each containing 100 ml of sterile seed medium consisting of the following ingredients:
Peptone: 5 g/l
Brewer's yeast: 3 g/l
Calcium nitrate: 0.5 g/l
Distilled Water: Balance The seed medium presterilization pH is 7.0. The seed inoculum is grown for about 48 hours at 28° C. on a Gump rotary shaker operating at 250 rpm and having a 2½ inch stroke.

Seed inoculum (inoculation rate can be from 5 to 10%), prepared as described above, is used to inoculate a series of 500-ml Erlenmeyer flasks each containing 100 ml of sterile medium consisting of the following ingredients:
Tryptone: 5 g/l
Yeast extract: 3 g/l
Glucose monohydrate: 20 g/l
Distilled Water: Balance The inoculated medium is incubated at a temperature of 25° C. while being agitated at a rate of 250 rpm on a Gump rotary shaker.

Between about 36 and 48 hours of fermentation time, steffimycin is added to the fermentation as a dimethylformamide solution (25 mg/ml) to a final medium concentration of 25 mg/l. The fermentation is monitored using tlc on silica gel plates with $CHCl_3:CH_3OH$ (925:75) as the developing solvent system. The tlc procedure is conducted at half day intervals between the first half day and five days.

Part B. Recovery

Fermentation beer (3.45 liters), as described above, is filtered and the filter cake is washed with 350 ml of water.

The filtrate is extracted with two 1-liter portions of $CH_2Cl_2$, and the filter cake is extracted with four 500-ml portions of $CH_2Cl_2$. Evaporation of the filtrate extracts in vacuo gives 740 mg of orange oil. Evaporation of the cake extracts in vacuo gives 23 mg of residue. A tlc in $CHCl_3$—$CH_3OH$ (9:1) indicates the two isolates were much the same containing a substantial portion of steffimycin ($R_f$ 0.42) and a lesser amount of 10-dihydrosteffimycin ($R_f$ 0.26). The mycelial extract is combined with 78 mg from previous similar fermentations and purified by preparative tlc using the above solvent system. The material from the filtrate is combined with material from a previous fermentation to give 1.65 g which was chromatographed on silica in a 30-ml suction funnel. The silica is washed with $CH_2Cl_2$, $CH_2Cl_2$—$CH_3OH$ (98:2), $CH_2Cl_2$—$CH_3OH$ (97:3), and $CH_2Cl_2$—MeOH (9:1). The fractions from the two chromatographies containing 10-dihydrosteffimycin as indicated by tlc are combined in two lots, one being without steffimycin and the other containing steffimycin. Each material is purified by preparative tlc using $CHCl_3$—$CH_3OH$ (9:1). The 10-dihydrosteffimycin fractions from these are combined and again chromatographed using preparative tlc with the same solvent system. The 10-dihydrosteffimycin fractions are isolated, combined, dissolved in $CH_2Cl_2$, and precipitated with a mixed hexane solvent to give an essentially pure preparation of 10-dihydrosteffimycin. The properties are: IR (nujol) 3360, 1670, 1615, 1595, 1565, 1460, 1405, 1385, 1370, 1310, 1290, 1245, 1205, 1160, 1135, 1105, 1085, 1055, 1040, 955, 780, 755 cm$^{-1}$; $^{13}$C NMR ($d_6$-DMSO) 190.1 (C-5), 181.0 (C-12), 166.2 (C-2), 164.5 (C-4), 161.1 (C-6), 149.4 (C-10a), 135.0 (C-11a), 137.0 (C-12a), 130.0 (C-6a), 117.4 (C-5a), 113.8 (C-11), 110.0 (C-4a), 107.6 (C-1), 106.0 (C-3), 70.4 (C-7), 85.5 (C-8), 73.5 (C-9), 70.6 (C-10), 100.9 (C-1'), 80.8 (C-2'), 70.5 (C-3'), 71.9 (C-4'), 69.9 (C-5'), 59.0, 58.5, 56.3 (3CH$_3$O), 18.6 (CH$_3$ at C-9), 17.8 (CH$_3$ at C-5'), mass spectrum (m/e) 400 (aglycone+H).

EXAMPLE 2—Bioconversion Of Steffimycin B To 10-Dihydrosteffimycin B

Part A. Fermentation

The microorganism Chaetomium sp. (BB 427), NRRL 11442 is maintained in a sterile soil. This biologically pure culture is used to inoculate a series of 500-ml Erlenmeyer flasks, each containing 100 ml of sterile seed medium consisting of the following ingredients:
Peptone: 5 g/l
Brewer's yeast: 3 g/l
Calcium nitrate: 0.5 g/l
Distilled Water: Balance The seed medium presterilization pH is 7.0. The seed inoculum is grown for about 48 hours at 28° C. on a Gump rotary shaker operating at 250 rpm and having a 2½ inch stroke.

Seed inoculum (inoculation rate can be from 5 to 10%), prepared as described above, is used to inoculate a series of 500-ml Erlenmeyer flasks each containing 100 ml of sterile medium consisting of the following ingredients:
Tryptone: 5 g/l
Yeast extract: 3 g/l
Glucose monohydrate: 20 g/l
Distilled water: Balance The inoculated medium is incubated at a temperature of 25° C. while being agitated at a rate of 250 rpm on a Gump rotary shaker.

Between about 36 and 48 hours of fermentation time, steffimycin B is added to the fermentation as a dimethylformamide solution (25 mg/ml) to a final medium concentration of 25 mg/l. The fermentation is monitored using tlc on silica gel plates with $CHCl_3:CH_3OH$ (925:75) as the developing solvent system. The tlc procedure is conducted at half day intervals between the first half day and five days.

Part B. Recovery

Fermentation beer (11.5 liters), as described above, to which 300 mg of steffimycin B has been added, is filtered.

The filter cake is washed with 1 liter of water which is added to the clear filtrate making a total of 12 liters. Both the filtrate and the filter cake are extracted with four 3-liter portions of methylene chloride. All of the extracts are combined and evaporated to dryness under reduced pressure. The residue weighs 1.50 g. The residue is chromatographed on 150 g of silica gel starting out with chloroform-methanol (98:2) and collecting 239 ten-ml fractions. The solvent is changed to 95:5 and a total of 575 fractions are collected. On the basis of tlc ($SiO_2$, $CHCl_3$—$CH_3OH$; 9:1) and a color maximum fractions 146-265 are combined. Evaporation of these fractions under reduced pressure gives 238 mg of residue. Recrystallization from acetone gives 98 mg of essentially pure 10-dihydrosteffimycin B. The filtrate is evaporated to dryness under reduced pressure, and the residue is chromatographed on 15 g of silica gel in chloroform-methanol (97:3) collecting 59 five-ml fractions. On the basis of a tlc comparison with the crystalline 10-dihydrosteffimycin B material; fractions 14-26 are combined and evaporated to dryness under reduced pressure to give 61 mg of residue which is combined with the crystalline material to give an essentially pure preparation of 10-dihydrosteffimycin B. For analytical purposes, a sample is recrystallized from acetone: mp 245-248 dec; $R_f$ 0.46 (tlc, $CHCl_3$—$CH_3OH$; 9:1); uv (EtOH) λ max 227 nm (ε 32,450), 267 (ε 18,760), 285 (ε 15,930), 430 (ε 12,500); ir (nujol) 3360, 1665, 1615, 1595, 1555, 1450, 1405, 1370, 1290, 1235, 1200, 1155, 1100, 1085, 1025, 950, 750 cm$^{-1}$; $^1$H NMR ($d_7$-DMF-$D_2O$) δ 1.27 (s, 3H, $CH_3C$), δ 1.30 (d, 3H, J=8 Hz, $CH_3CH$), δ3.60 (s, 3H, $CH_3O$), δ 3.67 (s, 3H, $CH_3O$), δ 3.97 (s, 3H, $CH_3O$), δ 4.87 (d, 2H, CHO), δ 5.45 (broad s, 1H, anomeric), δ 6.62 (d, 1H, H-3), δ 7.02 (d, 1H, H-1), δ 7.97 (s, 1H, H-11); $^{13}$C NMR ($d_6$-DMSO) δ 191.5 (C-5), δ 1.82.2 (C-12), δ 167.8 (C-2), δ 166.0 (C-4), δ 162.8 (C-6), δ 151.0 (C-10a), δ 136.2 (C-11a), δ 133.3 (C-12a), δ 130.3 (C-6a), δ 118.2 (C-5a), δ 115.0 (C-11), δ 111.3 (C-4a), δ 109.8 (C-1), δ 108.6 (C-3), δ 71.9 (C-7), δ 87.3 (C-8), δ 75.2 (C-9), δ 72.1 (C-10), δ 57.8 ($CH_3O$ at C-2), δ 60.7 ($CH_3O$ at C-8), δ 20.2 ($CH_3$ at C-9), 102.9 (C-1'), 82.7 (C-2'), 73.5 (C-3'), 84.1 (C-4'), 70.0 (C-5'), 19.4 ($CH_3$ at C-5'); mass spectrum (m/e) 400.1179, calculated for $C_{21}H_{20}O_8$, 400.1158 (aglycone+H).

Anal. Calcd. for $C_{29}H_{34}O_{13}$: C, 58.97; H, 5.80. Found: C, 58.31; H, 5.96.

EXAMPLE 3—Bioconversion Of Steffimycin B To 10-Dihydrosteffimycin B

A. Fermentation

The microorganism *Actinoplanes utahensis*, NRRL 5614, is maintained in a sterile soil. This biologically pure culture is used to inoculate a series of 500-ml Erlenmeyer flasks, each containing 100 ml of sterile seed medium consisting of the following ingredients:
Peptone: 5 g/l
Brewer's yeast: 3 g/l
Calcium nitrate: 0.5 g/l
Distilled water: Balance The seed medium presterilization pH is 7.0. The seed inoculum is grown for about 48 hours at 28° C. on a Gump rotary shaker operating at 250 rpm and having a 2½ inch stroke.

Seed inoculum (inoculation rate can be from 5 to 10%), prepared as described above, is used to inoculate a series of 500-ml Erlenmeyer flasks each containing 100 ml of sterile medium consisting of the following ingredients:
Tryptone: 5 g/l
Yeast extract: 3 g/l
Glucose monohydrate: 20 g/l
Distilled water: Balance The inoculated medium is incubated at a temperature of 25° C. while being agitated at a rate of 250 rpm on a Gump rotary shaker.

Between about 36 and 48 hours of fermentation time, steffimycin B is added to the fermentation as a dimethylformamide solution (25 mg/ml) to a final medium concentration of 25 mg/l. The fermentation is monitored using tlc on silica gel plates with $CHCl_3:CH_3OH$ (925:75) as the developing solvent system. The tlc procedure is conducted at half day intervals between the first half day and five days.

B. Recovery

The desired product, 10-dihydrosteffimycin B, is recovered from the fermentation beer by following the procedures disclosed in Example 2.

EXAMPLE 4—Acylates Of 10-Dihydrosteffimycin And 10-Dihydrosteffimycin B

10-Dihydrosteffimycin and 10-dihydrosteffimycin B can be acylated under standard acylating conditions with an appropriate acid halide or anhydride to give acylated compounds. The acylation of these compounds takes place at the following positions: 4, 6, 10, and 3' for 10-dihydrosteffimycin B and 4, 6, 10, 3' and 4' for 10-dihydrosteffimycin.

The acylation is carried out in the presence of an acid-binding agent. Suitable acid-binding agents include: amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, terbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, hydroxy-, amino-, cyano-, thiocyano-, and lower alkoxy- hydrocarbon carboxylic acids include hydrocarboncarboxylic acids as given above which are substituted by one or more of halogen, nitro, hydroxy, amino, cyano, or thiocyano, or lower alkoxy, advantageously lower alkoxy of not more than six carbon atoms, for example, methoxy, ethoxy, propoxy, butoxy, amyloxy, hexyloxy groups and isomeric forms thereof. Examples of such substituted hydrocarbon carboxylic acids are:

mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methylcyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicyclic acid;
p-hydroxybenzoic acid;
β-resorcyclic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate);
and the like.

The acylated compounds, as described above, can be used in animals for the same biological purposes as disclosed above for steffimycin and steffimycin B. For example, the acylated compounds can be given in oral form to an animal possessing the necessary enzyme to remove the acyl group, thus freeing the parent antibiotic compound which then inhibits susceptible bacteria.

10-Dihydrosteffimycin and 10-dihydrosteffimycin B form salts with alkali metals and alkaline earth metals. Metal salts can be prepared by dissolving 10-dihydrosteffimycin or 10-dihydrosteffimycin B in methanol, adding a dilute metal base until the pH of the solution is about 9 to 11, and freeze drying the solution to provide a dried residue consisting of the metal salt. Metal salts can be, for example, the sodium, potassium and calcium salts.

10-Dihydrosteffimycin and 10-dihydrosteffimycin B salts, as described above, can be used for the same antibacterial purposes as 10-dihydrosteffimycin and 10-dihydrosteffimycin B.

The lower alkyl ethers, i.e., 1 to 4 carbon atoms, inclusive, of the phenolic hydroxyl groups on both 10-dihydrosteffimycin and 10-dihydrosteffimycin B can be prepared by methods well known in the art. For example, the methyl ether can be prepared by reacting the antibiotics with dimethylsulfate and potassium carbonate in an acetone solution at room temperature for about 24 hours. The desired product can be recovered from the reaction mixture by evaporation of the acetone and partitioning of the residue between dilute base and chloroform or ethyl acetate. Evaporation of the organic phase followed by chromatography on silica gel using $CHCl_3$—MeOH (97:3 v/v) as the solvent system, gives the pure ether.

The above ethers can be used for the same antibacterial purposes as the parent compounds.

The compounds of the subject invention have the following antimicrobial spectrum in comparison with steffimycin and steffimycin B. The tests were conducted on a standard disc (6 mm) plate assay. The compound to be tested is used to saturate a disc at a concentration of 1 mg/ml.

| Test Microorganism | Drug Tested (6 mm disc saturated with drug at 1 mg/ml) | Zone Of Inhibition (mm) |
| --- | --- | --- |
| Bacillus subtilis, UC® 564 | Steffimycin B | 25 |
| | 10-Dihydrosteffimycin B | 13 |
| | Steffimycin | 25 |
| | 10-Dihydrosteffimycin | 12 |
| | Control - Untreated Disc Only | 0 |
| Bacillus subtilis, UC® 564, Synthetic Medium | Steffimycin B | 33 |
| | 10-Dihydrosteffimycin B | 17 |
| | Steffimycin | 32 |
| | 10-Dihydrosteffimycin | 14 |

| Test Microorganism | Drug Tested (6 mm disc saturated with drug at 1 mg/ml) | Zone Of Inhibition (mm) |
|---|---|---|
| | Control - Untreated Disc | 0 |
| Bacillus cereus, UC® 3145 | Steffimycin B | 17 |
| | 10-Dihydrosteffimycin B | 25 hazy |
| | Steffimycin | 19 |
| | 10-Dihydrosteffimycin | 30 hazy |
| | Control - Untreated Disc | 2 |
| Sarcina lutea, UC® 130 | Steffimycin B | 24 |
| | 10-Dihydrosteffimycin B | 10 |
| | Steffimycin | 27 |
| | 10-Dihydrosteffimycin | 13 |
| | Control | 0 |
| Sarcina lutea (sens)-124 | Steffimycin B | 30 |
| | 10-Dihydrosteffimycin B | 13 |
| | Steffimycin | 34 |
| | 10-Dihydrosteffimycin | 18 |
| | Control - Untreated Disc | 0 |
| Staphylococcus aureus, UC® 80 | Steffimycin B | 16 |
| | 10-Dihydrosteffimycin B | 13 hazy |
| | Steffimycin | 18 |
| | 10-Dihydrosteffimycin | 13 hazy |
| | Control - Untreated Disc | 0 |
| Streptococcus pyrogenes, UC® 6055 | Steffimycin B | 20 |
| | 10-Dihydrosteffimycin B | 15 |
| | Steffimycin | 21 |
| | 10-Dihydrosteffimycin | 15 |
| | Control - Untreated Disc | 0 |
| Mycobacterium avium, UC® 159 | Steffimycin B | 35 |
| | 10-Dihydrosteffimycin B | 17 |
| | Steffimycin | 28 |
| | 10-Dihydrosteffimycin | 18 |
| | Control - Untreated Disc | 0 |

None of the drugs tested were active vs. *Escherichia coli*, UC® 51, *E. coli*, UC® 51 (synthetic medium); *Pseudomonas aeruginosa*, UC® 95; *Pseudomonas mildenbergii*, UC® 3026; *Proteus vulgaris*, UC® 93; *Klebsiella pneumoniae*, UC® 57, *Salmonella gallinarum*, UC® 265; *Salmonella schottmuelleri*, UC® 126; *Rhodopseudomonas sphaeroides*, UC® 3238; *Penicillium oxalicum*, UC® 1268; *Saccharomyces cervisiae*, UC® 1337; and *Saccharomyces pastorianus*, UC® 1342.

"UC" is a registered trademark of The Upjohn Company Culture Collection.

The above data shows the activity of the novel compounds of the invention against various Gram-positive bacteria. For example, they are active against *Bacillus subtilis*, *Bacillus cereus*, *Staphylococcus aureus*, *Sarcina lutea*, and *Mycobacterium avium*. Accordingly, these compounds can be used as a disinfectant on washed and stacked food utensils contaminated with *Staphylococcus aureus*. They can also be used in birds and rabbits to control the organism *Mycobacterium avium* which is a known producer of generalized tuberculosis in these animals. They can also be used in papermill operations to control the contamination of wool by the organism *Bacillus cereus*. They can also be used in petroleum products storage to control the microorganism *Bacillus subtilis* which is a known slime and corrosion producer in petroleum products storage.

We claim:
1. 10-Dihydrosteffimycin, a compound having the following structure:

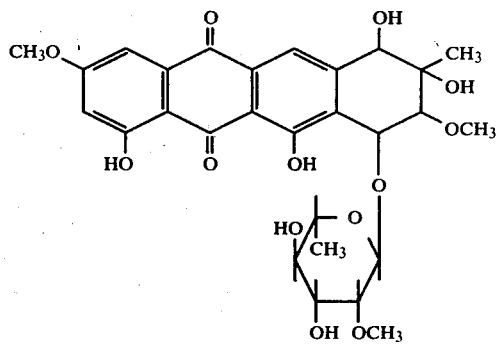

and alkali and alkaline earth metal salts thereof.

2. 10-Dihydrosteffimycin B, a compound having the following structure:

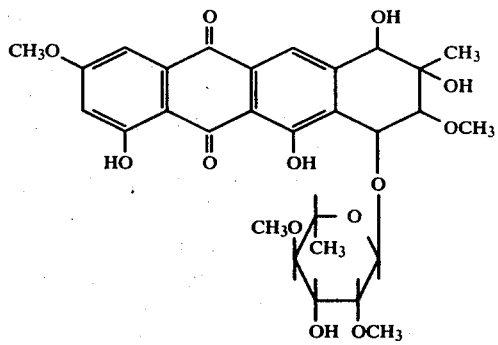

and alkali and alkaline earth metal salts thereof.

3. Penta-O-acylates of the compound defined in claim 1 wherein said acyl group consists of a hydrocarbon carboxylic acid acyl of from 2 to 18 carbon atoms, inclusive; halo-, nitro-, hydroxy-, amino-, cyano-, thiocyano-, and lower alkoxy-substituted hydrocarbon carboxylic acid acyl of from 2 to 18 carbon atoms, inclusive.

4. Tetra-O-acylates of the compound defined in claim 2 wherein said acyl group consists of a hydrocarbon carboxylic acid acyl of from 2 to 18 carbon atoms, inclusive; halo-, hydroxy-, amino-, cyano-, thiocyano-, and lower alkoxy-substituted hydrocarbon carboxylic acid acyl of from 2 to 18 carbon atoms, inclusive.

5. The 4,6-di-O- lower alkyl ether of 10-dihydrosteffimycin, the compound defined in claim 1.

6. A compound, according to claim 5, wherein said lower alkyl is methyl.

7. The 4,6-di-O- lower alkyl ether of 10-dihydrosteffimycin B, the compound defined in claim 2.

8. A compound, according to claim 7, wherein said lower alkyl is methyl.

* * * * *

UNITED STATES PATENT AND TRADEMARK OFFICE
CERTIFICATE OF CORRECTION

PATENT NO. : 4,209,611
DATED : June 24, 1980
INVENTOR(S) : Vincent P. Marshall, David W. Elrod, Paul F. Wiley It is certified that error appears in the above-identified patent and that said Letters Patent are hereby corrected as shown below:

Column 4, line 29: "is an" should read --in an--.
Column 5, line 9 : "(25 mg/I)" should read --(25 mg/1)--.
Column 11, line 24: "pyrogenes" should read --pyogenes--.
Column 12, line 47: "halo-, hydroxy-," should read --halo-, nitro-, hydroxy-,--

Signed and Sealed this

Seventh Day of October 1980

[SEAL]

Attest:

SIDNEY A. DIAMOND

Attesting Officer

Commissioner of Patents and Trademarks